United States Patent [19]
Muto et al.

[11] Patent Number: 5,852,057
[45] Date of Patent: Dec. 22, 1998

[54] ANTICARCINOGENIC DRUG COMPOSITION

[75] Inventors: Yasutoshi Muto; Hisataka Moriwaki, both of Gifu; Mitsuo Ninomiya, Gifu-ken; Sadashi Adachi, Takayama; Akiko Saito; Takeshi Takasaki, both of Tokyo; Takuji Tanaka, Gifu; Kaito Tsurumi, Gifu; Masataka Okuno, Gifu; Eiichi Tomita, Gifu; Toshiyuki Nakamura, Gifu; Takao Kojima, Gifu, all of Japan

[73] Assignee: Yasutoshi Muto, Gifu, Japan

[21] Appl. No.: 819,321

[22] Filed: Mar. 18, 1997

[30] Foreign Application Priority Data

Dec. 12, 1996 [JP] Japan .................................. 8-331816

[51] Int. Cl.$^6$ .................................................. A61K 31/20
[52] U.S. Cl. .............................................................. 514/560
[58] Field of Search ............................................. 514/560

[56] References Cited

U.S. PATENT DOCUMENTS 4,988,732  1/1991  Yamatsu et al. ........................ 514/560

FOREIGN PATENT DOCUMENTS 0 614 662  9/1994  European Pat. Off. .

OTHER PUBLICATIONS

Database WPIL, Derwent Publications, AN 86–267856, JP 61–194018, Aug. 28, 1986.

Database WPIL, Derwent Publications, AN 86–082985, EP 0175171, Mar. 26, 1986.

Database WPIL, Derwent Publications, AN 84–115750, EP 0107188, May 2, 1984.

Database WPIL, Derwent Publications, AN–81–60469D, BE 888290, Jul. 31, 1981.

Database WPIL, Derwent Publications, AN 83–784326, EP 0090378, Oct. 5, 1983.

*Primary Examiner*—Jerome D. Goldberg
*Attorney, Agent, or Firm*—Oblon, Spivak, McClelland, Maier & Neustadt, P.C.

[57] ABSTRACT

The invention provides an anticarcinogenic drug composition which effectively inhibits the recurrence of hepatocellular carcinoma (the occurrence of second primary tumor), the occurrence of hepatocellular carcinoma in high risk groups with chronic hepatitis and liver cirrhosis, the occurrence of cervical carcinoma intraepitheliale, lung adenocarcinoma, lung squamous cell carcinoma, mammary tumor, and the like and is highly safe. The anticarcinogenic drug composition contains 3,7,11,15-tetramethyl-2,4,6,10,14-hexadecapentaenoic acid or a salt thereof.

5 Claims, 1 Drawing Sheet

ANTICARCINOGENIC DRUG COMPOSITION

BACKGROUND OF THE INVENTION

1. Field of the Invention

The present invention relates to an anticarcinogenic drug composition, especially to an anticarcinogenic drug composition which effectively prevents the recurrence of hepatocellular carcinoma, the occurrence of hepatocellular carcinoma (hepatoma) in high risk groups with chronic hepatitis and liver cirrhosis, and the occurrence of cervical carcinoma intraepitheliale, lung adenocarcinoma, lung squamous cell carcinoma, mammary tumors, and the like, in cell lines of the carcinoma, and is highly safe.

2. Discussion of the Background

The hepatitis virus (type B and type C) is believed to be the etiological agent of hepatocellular carcinoma, and hepatocellular carcinoma is associated with successively infectious hepatitis virus in 90 percent of patients, by which chronic hepatitis is pathologically changed to hepatocellular carcinoma via liver cirrhosis. A vaccine for the hepatitis B virus has recently been developed. However, no vaccine has been developed for the hepatitis C virus. Also, the complete cure rate for curative treatment using preparations of interferon barely reaches 30 percent. At the present time, no decisive treatment has been found for hepatocellular carcinoma.

Conventionally, patients with hepatocellular carcinoma are treated with surgical resection or regionally percutaneous injection of ethanol therapy. A radical cure is achieved by these treatments, but it is temporary. The rate of recurrence of hepatocellular carcinoma (the occurrence of a second primary tumor) is high at present.

This is because the hepatocellular carcinoma, in contradistinction to the carcinomas of other organs, e.g. carcinoma in the stomach, acquires multicentric carcinogenesis, by which precancerous lesions, that is, carcinogenic mother fields are produced (field cancerization) over a wide area, and, hence, the recurrence of hepatocellular carcinoma (the occurrence of a second primary tumor) is not effectively prevented by treatment by conventionally surgical resection and regionally percutaneous injection therapy. Also, for high risk groups with chronic hepatitis and liver cirrhosis, the carcinogenic mother fields are produced over a wide area in the same manner as above, so that the recurrence of hepatocellular carcinoma can be prevented only with difficulty.

In addition, there are safety problems in the use of a variety of chemotherapies and radiotherapy because these therapies inevitably involve severe side effects. Specifically, because generally known anticancer drugs inhibit the proliferation of existing cancer (inhibit the synthesis of DNA), these drugs act partially on the host, leading to the occurrence of catastrophic side effects.

SUMMARY OF THE INVENTION

The present invention has been achieved in view of this situation and has an object of providing an anticarcinogenic drug which effectively prevents the recurrence of hepatocellular carcinoma (the occurrence of a second primary tumor) and occurrence of hepatocellular carcinoma in high risk groups with chronic hepatitis and liver cirrhosis, and is highly safe.

This object is attained by the present invention which provides an anticarcinogenic drug or pharmaceutical composition comprising as an active component an effective amount of 3,7,11,15-tetramethyl-2,4,6,10,14-hexadecapentazenoic acid illustrated in the following formula,

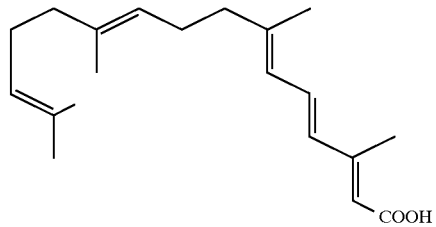

or a salt thereof and a pharmaceutically acceptable carrier.

Other objects, features and advantages of the invention will hereinafter become more readily apparent from the following description.

DETAILED DESCRIPTION OF THE PREFERRED EMBODIMENTS

Figure 1:
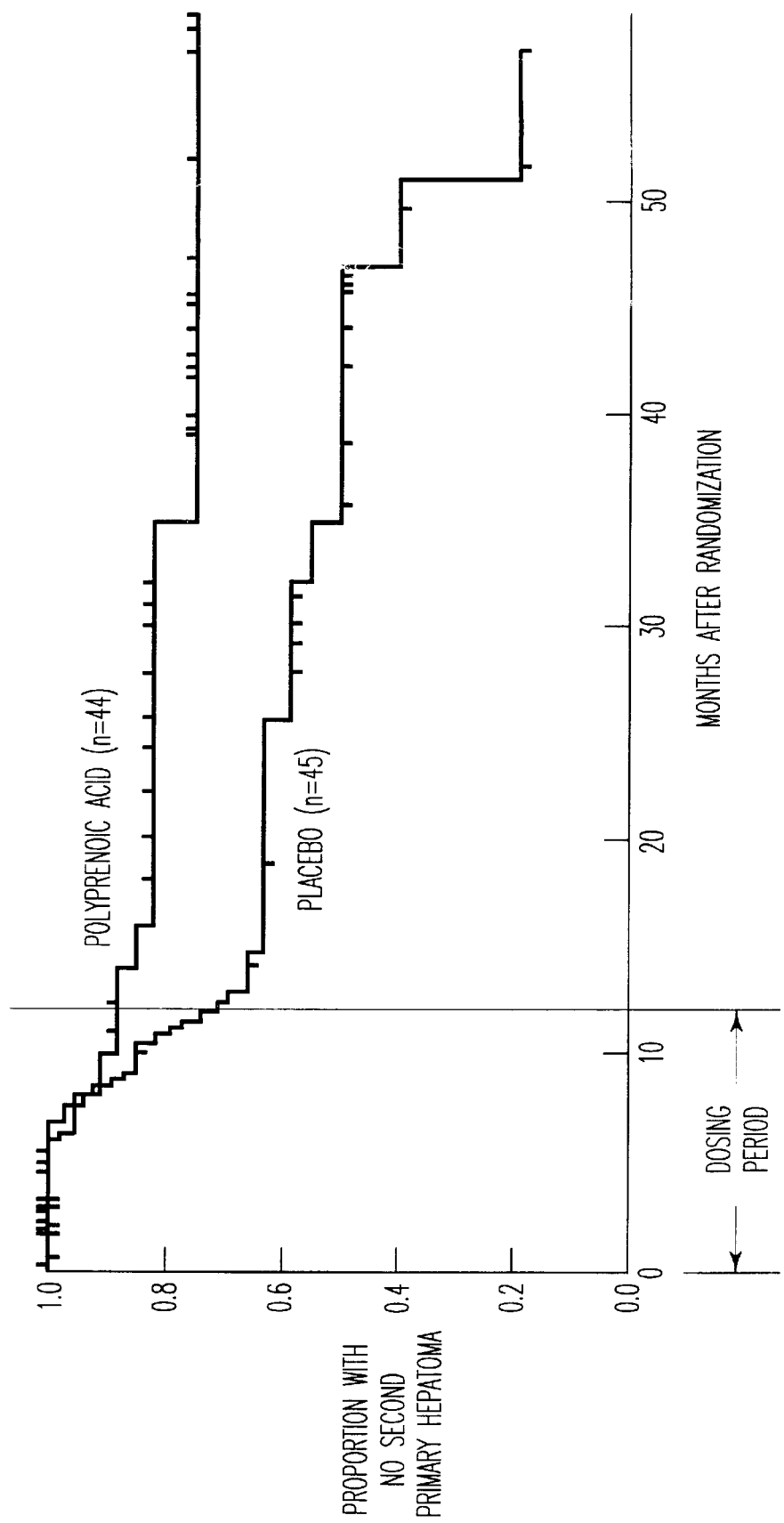
FIG. 1 is a graph showing Kaplan-Meier estimates of the proportion of patients without the recurrence of hepatocellular carcinoma (the occurrence of second primary tumor) months after randomization (the beginning of examination).

A preferred embodiment of the present invention will now be explained in detail.

3,7,11,15-Tetramethyl-2,4,6,10,14-hexadecapentaenoic acid is an acyclic retinoid (polyprenoic acid) and is preferably contained as a major component (at least 50 wt %, preferably, at least 80 wt %) in the anticarcinogenic pharmaceutical composition of the present invention. 3,7,1,15-tetramethyl-2,4,6,10,14-hexadecapentaenoic acid is a crystalline powder with a white to lemon yellow color and is odorless. This compound functions to effectively prevent the recurrence of hepatocellular carcinoma (the occurrence of a second primary tumor), occurrence of hepatocellular carcinoma in high risk groups with chronic hepatitis and liver cirrhosis, and occurrence of cervical carcinoma intraepitheliale, lung adenocarcinoma, lung squamous cell carcinoma, mammary tumors, and the like, in cell lines of the carcinoma. The compound also has relatively low toxicity.

Any pharmaceutically acceptable salt of 3,7,11,15-tetramethyl-2,4,6,10,14-hexadecapentaenoic acid may also be used.

EXAMPLE

A pharmacological test and a toxicity test for the anticarcinogenic drug composition of the present invention and the results of these tests are described below. The primary object of these tests was to confirm the effect on the prevention of the recurrence of hepatocellular carcinoma. However, one skilled in this art would expect the same effects relative to the occurrence of hepatocellular carcinoma in high risk groups with chronic hepatitis and liver cirrhosis because its molecular mechanism is similar to that of the recurrence of hepatocellular carcinoma.

1. Pharmacological Test (I)

(1) Method

A double blind study for comparison was conducted according to the following procedure. Among 89 patients who had been treated by surgical resection or regionally percutaneous injection of ethanol therapy, 44 patients (a drug group) were assigned to receive the anticarcinogenic drug (sealed in a capsule) of the present invention and 45 patients (a placebo group) were assigned to receive a placebo (peanut oil only, sealed in a capsule) together orally at a dose of 600 mg per day for one year. Specifically, two capsules each containing 150 mg of the drug of the present invention were orally administered to each patient in the drug group twice a day.

In this test, the dosage of the drug of the present invention was 600 mg per day, which corresponded to 10 mg per 1 kg of patient body weight when the weight of patient was 60 kg. A preferable dosage of the drug of the present invention is about 1 to about 100 mg/kg. This was preferable in view of safety, since the drug of the present invention had an outstanding effect despite using such a small dosage.

As shown in Table 1, there were no statistically significant differences between the backgrounds of the human subjects (patients) with regard to the factors of age, sex, cause and activity of hepatocellular carcinoma, number and size of primary hepatomas, and type of primary treatment. Also, the human subjects were well randomized.

TABLE 1

Demographic and clinical characteristics of the human subjects on entering the study

| Chracteristic | Drug Group (N = 44) | Placebo Group (N = 45) |
|---|---|---|
| Sex (male/female) | 32/12 | 36/9 |
| Age (Year) | 62 ± 8* | 60 ± 8 |
| Cause of hepatocellular carcinoma (no. of patients) | | |
| Hepatitis B virus | 5 | 7 |
| Hepatitis C virus | 32 | 35 |
| Other (including alcoholism) | 7 | 3 |
| Hepatomas treated | | |
| No | 1.5 ± 0.5 | 1.4 ± 0.5 |
| Maximum diameter (cm) | 2.9 ± 1.2 | 3.0 ± 1.3 |
| Treatment method (no. of patients) | | |
| Surgical resection | 33 | 36 |
| Ethanol injection | 11 | 9 |
| Clinical stage (no. of patients) | | |
| I | 28 | 33 |
| II | 14 | 9 |
| III | 2 | 3 |
| Plasma alanine aminotransferase (IU/liter) | 65 ± 21 | 68 ± 23 |
| Plasma alpha-fetoprotein (AFP) (ng/ml) | 38 ± 22 | 37 ± 21 |
| Plasma retinol (μg/ml) | 8.9 ± 1.1 | 8.7 ± 1.3 |

*Plus-minus values are means ± standard deviation (2) Test Results

An evaluation of the tests was carried out to identify cases where hepatocellular carcinoma with a diameter mostly between 7 mm and 30 mm was observed using ultrasonography or CT examination for the recurrence of hepatocellular carcinoma. In the examination, the liver of the subject was separated into eight regions to be examined. The rate of recurrence of hepatocellular carcinoma (the rate of treatment failure) is shown in Table 2.

Treatment with polyprenoic acid significantly reduced the incidence of recurrent or new hepatocellular carcinomas. After a median follow-up of 38 months, 12 patients (27 percent) in the drug group had recurrent or new hepatocellular carcinoma as compared with 22 patients (49 percent) in the placebo group (significant level P=0.04).

The greatest difference was that the second primary tumors were observed in 7 patients (16 percent) in the group receiving the drug of the present invention as compared with 20 patients (44 percent) in the placebo group (P=0.004). In this case, 27 second primary tumors in 27 patients in which a second primary tumor was found occurred in a liver segment different from the original liver segment having a tumor. These tumors were all determined to be very well differentiated hepatocellular carcinomas by histological examination.

Cox proportional hazard analysis demonstrated that only the drug of the present invention was an independent factor and reduced the occurrence of second primary tumors. Here, the adjusted relative risk was 0.31 and the 95 percent confidence interval was 0.12 to 0.78. It was confirmed that the drug of the present invention reduced the occurrence of second primary tumors to less than ⅓.

TABLE 2

Incidence of Treatment Failure

| Type of recurrence of carcinoma | Drug group (N = 44) | Placebo group (N = 45) | P value* |
|---|---|---|---|
| | No. of patients (%) | | |
| Disease recurrence | 5 (11) | 2 (4) | 0.23 |
| Early (<6 mo) | 5 (11) | 2 (4) | 0.23 |
| Late (≧6 mo) | 0 | 0 | — |
| Distant metastasis | 0 | 0 | — |
| Second primary tumor | 7 (16) | 20 (44) | 0.004 |
| All | 12 (27) | 22 (49) | 0.04 |

*By the chi-square test without Yates' correction

2. Pharmacological Test (II)

(1) Method $10^4$ to $10^5$ cells/well of various cell lines of carcinomas were incubated at 37° C. in a culture medium (α-MEM solution, penicillin 50 μ/ml, streptomycin 50 mg/ml) overnight in the presence of 5% $CO_2$. After the incubation, the apoptosis of the cell lines was evaluated by the following two methods.

(1) A method in which the image of the cell lines concentrated by chromatin is dyed with a fluorescent dye (Hoechist 33253).

(2) A method in which DNA is prepared from floating or easily separable cells and the laddering pattern of the DNA is detected by means of electrophoresis with 2% agarose.

(2) Test Results

As shown in Table 3, the drug of the present invention induced apoptosis in the cell lines of 8 carcinomas. It was confirmed that the drug of the present invention was capable of inducing the apoptosis in various cell lines of carcinomas to effectively prevent the occurrence of carcinomas.

TABLE 3

| Cell lines of carcinoma | Apoptosis |
|---|---|
| Hepatocellular carcinoma | |
| PLC/PRF-5 | + |
| HuH-7 | + |
| cervical carcinoma intraepitheliale | |
| CICCL-2 | + |

TABLE 3-continued

| Cell lines of carcinoma | Apoptosis |
|---|---|
| Lung adenocarcinoma | |
| A 549 | + |
| Lung squamous cell carcinoma | |
| LK-2 | + |
| LS-1sq | + |
| Mammary tumor | |
| MMT | + |
| SH101 | + |

3. Toxicity Test

Each of 89 patients took at least one capsule containing polyprenoic acid as the drug of the present invention, or a placebo during the study, which included an analysis of the toxicity. One patient given polypreonic acid had a severe headache on the first day of therapy, and the drug was discontinued. In the placebo group, one patient had a severe skin eruption and one had moderate nausea, necessitating discontinuation of therapy in each. No typical toxic effects of retinoids, such as skin dryness, cheilitis, or conjunctivitis, were observed in either group, nor was there any toxicity possibly related to the laboratory diagnosis observed in either group. Also, no hypertriglyceridemia was induced in either group.

Only 5 (11 percent) of the 44 patients in the drug group could not complete the course of treatment. This was because 1 patient had a headache as mentioned above and 4 patients did not receive the drug. In the remaining 39 patients, except for 5 patients who stopped receiving the drug half way through, the mean plasma levels of polyprenoic acid reached 44.9±13.9 mg per milliliter one year after the beginning of therapy.

Six of the 45 patients in the placebo group discontinued therapy. Among these 6 patients, 2 discontinued therapy because of toxic effects and 4 because of non-reception of the drug.

As mentioned above, it was confirmed that the anticarcinogenic drug of the present invention had very low toxicity and could be continuously administered for as long a time duration as one year. From these facts, the anticarcinogenic drug of the present invention is seen to be remarkably safe when used as an agent for inhibiting the occurrence and recurrence of carcinomas.

4. Manufacturing Method

The polyprenic acid is known and there is no limitation regarding the method for manufacturing the anticarcinogenic drug of the present invention. For example, the method illustrated in Japanese Patent Publication No. 32058/1988 (corresponds to U.S. Pat. No. 4,988,732) can be used.

Also, there is no limitation on the method for pharmaceutical preparation of the drug of the present invention which may contain any known pharmaceutically acceptable carrier. The methods for preparing general capsules or tablets can be used.

As is clear from the above descriptions, the present invention provides an anticarcinogenic drug which effectively prevents the recurrence of hepatocellular carcinomas (the occurrence of a second primary tumor), occurrence of hepatocellular carcinoma in high risk groups with chronic hepatitis and liver cirrhosis, and occurrence of cervical carcinoma intraepitheliale, lung adenocarcinoma, lung squamous cell carcinoma, mammary tumors, and the like in cell lines of the carcinoma, and is highly safe. In other words, the anticarcinogenic drug of the present invention brings about eradication of the precancerous cells by either apoptosis or differentiation and induction and does not act on normal cells or noncancerous cells. Hence, the effect of the anticarcinogenic drug of the present invention is improved after discontinuation of administration rather than before so that the anticarcinogenic drug of the present invention can continuously exhibit high prevention of the recurrence of carcinomas for as long as four years.

Japanese priority application no. H8(1996)-331816 filed Dec. 12, 1996, is incorporated herein by reference in its entirety.

obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method for preventing the recurrence of hepatocellular carcinoma or the occurrence of hepatocellular carcinoma in a patient with chronic hepatitis or liver cirrhosis comprising administering to a patient an effective amount of a medicant comprising 3, 7, 11, 15-tetramethyl-2,4,6,10,14-hexadecapentaenoic acid or a salt thereof.

2. The method according to claim 1, wherein the amount of said acid or salt thereof is from about 1 to 100 mg/kg.

3. A method for inducing apoptosis in hepatocellular carcinoma cells comprising administering to said cells an effective amount of 3, 7, 11, 15-tetramethyl-2,4,6,10,14-hexadecapentaenoic acid or a salt thereof.

4. The method according to claim 3, wherein the amount of said acid or salt thereof is from 1 to 10 mg/kg.

5. The method according to claim 3, wherein said cells are in a human patient and the acid or salt is administered orally or by injection.

* * * * *